(12) United States Patent
Zhang et al.

(10) Patent No.: US 8,134,128 B2
(45) Date of Patent: *Mar. 13, 2012

(54) METHOD AND SYSTEM FOR PLASMA-INDUCED TERAHERTZ SPECTROSCOPY

(75) Inventors: Xi-Cheng Zhang, Melrose, NY (US); Jianming Dai, Troy, NY (US); Xu Xie, Berkeley, CA (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/634,282

(22) Filed: Dec. 9, 2009

(65) Prior Publication Data

US 2010/0277718 A1    Nov. 4, 2010

Related U.S. Application Data

(62) Division of application No. 11/835,152, filed on Aug. 7, 2007, now Pat. No. 7,652,253.

(60) Provisional application No. 60/891,438, filed on Feb. 23, 2007.

(51) Int. Cl.
*G01J 5/02* (2006.01)

(52) U.S. Cl. .................................................. 250/341.1

(58) Field of Classification Search ................ 250/341.1
See application file for complete search history.

(56) References Cited

U.S. PATENT DOCUMENTS

| 4,854,710 A * | 8/1989 | Opsal et al. ............... 356/432 |
| 2005/0230625 A1* | 10/2005 | Zhang et al. ............... 250/341.1 |

OTHER PUBLICATIONS

Bauer et al., "Mid-infrared Lidar for Remote Detection of Explosives," 2006, H. Schubert and A. Rimski-Korsakov (eds.), Stand-off Detection of Suicide Bombers and Mobile Subjects, pp. 127-133.*
Dai et al., "Detection of Broadband Terahertz Waves with Laser-induced Plasma in Gases," Physical Review Letters, 97, 103903, 2006 (22 pages), Sep. 8, 2006.
Xie et al., "Coherent Control of THz Wave Generation in Ambient Air," Physical Review Letters, 96, 075005, The American Physical Society, Feb. 24, 2006 (4 pages).
Zhong et al., "Terahertz Emission Profile From Laser-Induced-Air-Plasma," Applied Physics Letters, 88, 261103, 2006 (14 pages).
Zhong et al., "THz Wave Standoff Detection of Explosive Materials", Proc. SPIE, 6212, 62120, 2006.
Zhong et al., "Identification and Classification of Chemicals Using Terahertz Reflective Spectroscopic Focal-plane Imaging System", Opt. Expr., 14, 9130-9141, 2006.

* cited by examiner

*Primary Examiner* — David Porta
*Assistant Examiner* — Carolyn Igyarto
(74) *Attorney, Agent, or Firm* — Heslin Rothenberg Farley & Mesiti P.C.

(57) ABSTRACT

A method of analyzing a remotely-located object includes the step of illuminating at least a portion of a targeted object with electromagnetic radiation to induce a phase transformation in the targeted object, wherein the phase transformation produces an emitter plasma, which emits terahertz radiation. The method also includes the step of ionizing a volume of an ambient gas to produce a sensor plasma by focusing an optical probe beam in the volume and the step of detecting an optical component of resultant radiation produced from an interaction of the focused optical probe beam and the terahertz radiation in the sensor plasma. Detecting an optical component of the resultant radiation emitted by the sensor plasma facilitates detection of a characteristic fingerprint of the targeted object imposed onto the terahertz radiation produced as a result of the induced phase transformation.

19 Claims, 7 Drawing Sheets

METHOD AND SYSTEM FOR PLASMA-INDUCED TERAHERTZ SPECTROSCOPY

CROSS-REFERENCE TO RELATED APPLICATIONS

This application is a division of U.S. Ser. No. 11/835,152, filed on Aug. 7, 2007, and claims priority under 35 U.S.C. §119 to U.S. Provisional Application No. 60/891,438 entitled "Method and System for Plasma-Induced Terahertz Spectroscopy", filed Feb. 23, 2007, which is herein incorporated by reference in its entirety.

GOVERNMENT RIGHTS STATEMENT

This invention was made with U.S. Government support under Grant No. ECS-0621522 from the National Science Foundation, Grant No. DAAD 19-02-1-0255 from the Army Research Office, and Grant No. N00014-06-1-0480 from the Naval Research Office. The U.S. Government has certain rights in the invention.

BACKGROUND OF THE INVENTION

1. Technical Field

The present invention generally relates to terahertz spectroscopy and, more particularly, to analyzing a remote, targeted object by detecting terahertz radiation that results from inducing a phase transformation in the targeted object.

2. Background Information

Improvised explosive devices (IEDs) are extremely dangerous partially because they are difficult to identify. A device capable of remote and in situ monitoring to detect concealed explosives would be very beneficial for a number of defense and homeland security uses.

Since terahertz wave spectroscopy has been utilized to detect a number of chemical and explosive materials and related compounds by providing their spectral signatures in the terahertz frequency range, it may have use in defense and security applications. For example, there is interest in terahertz wave spectroscopy as a technique to sense improvised explosive devices (IEDs). However, due to the severe water vapor attenuation of terahertz waves in the atmosphere, the reliable sensing range of terahertz wave spectroscopy has been limited to relatively short distances. For example, even though propagation of a pulsed terahertz wave for more than 145 meters has been achieved, spectroscopic measurement with an acceptable signal-to-noise ratio and false alarm rate is limited to about 30 meters. For defense and security applications, it is desirable to increase the reliable sensing range of terahertz wave spectroscopy. Thus, there is a need for a technique to increase the range at which terahertz waves may be reliably sensed under a range of atmospheric conditions and to decrease the sensitivity to the humidity level.

SUMMARY OF THE INVENTION

Briefly, the present invention satisfies the need for a technique that increases the range at which terahertz spectroscopy may be reliably utilized to analyze an object under a range of atmospheric conditions.

The present invention provides, in one aspect, a method of and system for analyzing a remotely-located object. The method includes the step of illuminating at least a portion of a targeted object with electromagnetic radiation to induce a phase transformation in the targeted object, wherein the phase transformation produces an emitter plasma, which emits terahertz radiation. The method also includes the step of ionizing a volume of an ambient gas to produce a sensor plasma by focusing an optical probe beam in the volume and the step of detecting an optical component of resultant radiation produced from an interaction of the focused optical probe beam and the terahertz radiation in the sensor plasma.

In another aspect, the present invention provides a method of and system for analyzing a remotely-located object that includes illuminating at least a portion of a targeted object with electromagnetic radiation to induce a phase transformation in the targeted object, wherein the phase transformation produces an emitter plasma, which emits terahertz radiation; focusing an optical probe beam in the emitter plasma; and detecting an optical component of resultant radiation produced from an interaction of the focused optical probe beam and the terahertz radiation in the emitter plasma.

These, and other objects, features and advantages of this invention will become apparent from the following detailed description of various aspects of the invention taken in conjunction with the accompanying drawings.

DETAILED DESCRIPTION

Figure 1:
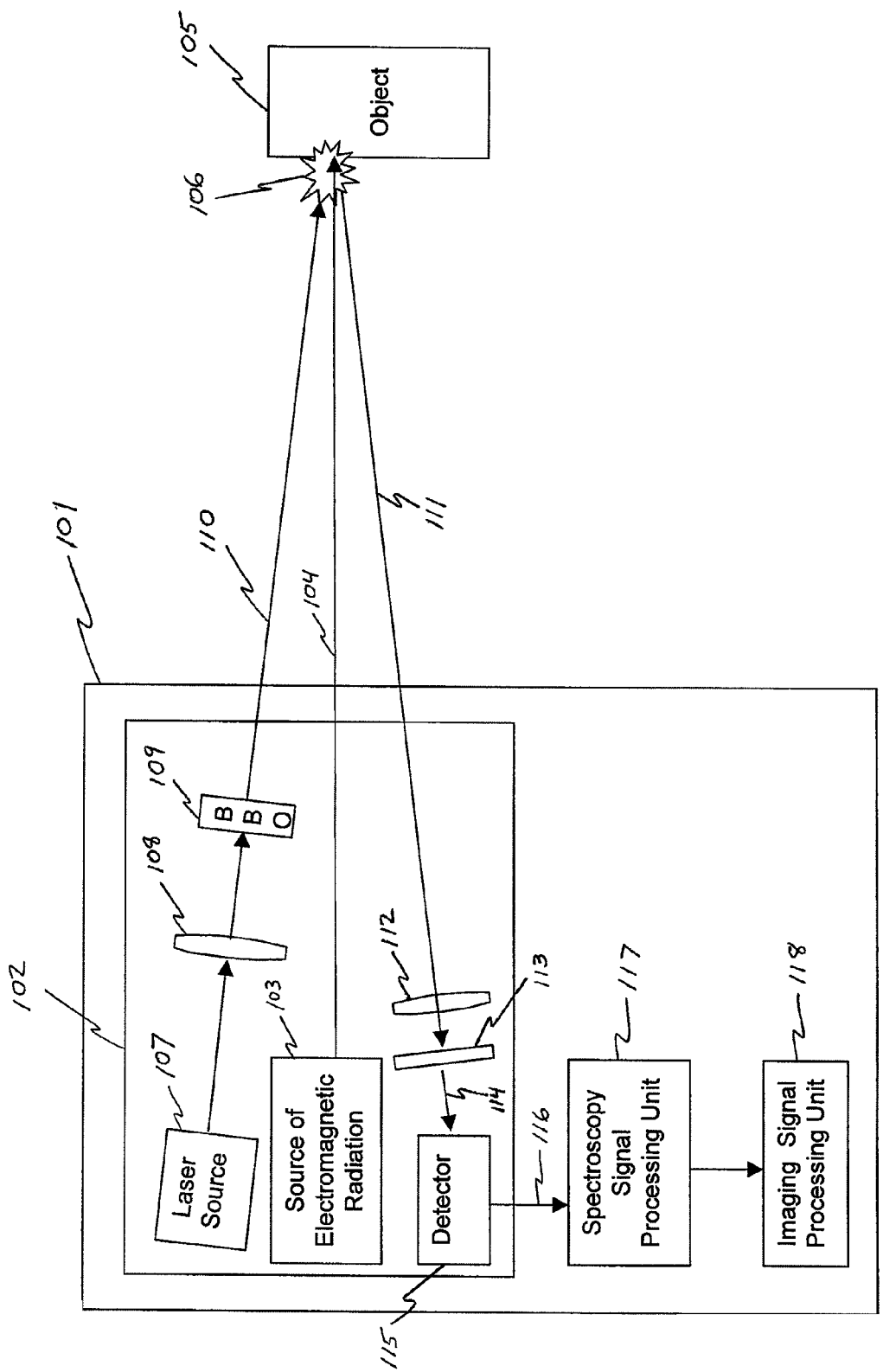
FIG. 1 illustrates one embodiment of a system for remotely analyzing an object, wherein an optical probe beam is focused in a plasma induced by illuminating at least a portion of a targeted object with electromagnetic radiation, in accordance with an aspect of the present invention.

The present invention provides, in one aspect, a method of and system for analyzing an object, which may be remotely located, wherein the method and system detect terahertz radiation emitted as a result of exciting at least a portion of the targeted object with electromagnetic radiation. The analysis of the targeted object utilizes the spectrum of the detected terahertz radiation. The method includes the step of illuminating at least a portion of a targeted object with electromagnetic radiation to induce a phase transformation in the targeted object, wherein the phase transformation produces an emitter plasma, which emits terahertz radiation. The spectrum of the terahertz radiation emitted by the resulting emitter plasma is characteristic of the substance or substances of the targeted object that has or have been ionized to produce the emitter plasma. The spectrum of the terahertz radiation emitted is manifested in an optical component of resultant radiation produced from an interaction of an optical probe beam and the terahertz radiation in a plasma. In one embodiment, the method also includes the step of ionizing a volume of an ambient gas to produce a sensor plasma by focusing the optical probe beam in the volume. Interaction of the focused optical probe beam and the terahertz radiation in the sensor plasma produces resultant radiation having an optical component. The method further includes detecting an optical component of the resultant radiation emitted by the sensor plasma.

In another embodiment, an optical probe beam interacts with the terahertz radiation in the emitter plasma. In this embodiment, an optical probe beam is focused in the emitter plasma, and an optical component of resultant radiation produced from an interaction of the focused optical probe beam and the terahertz radiation in the emitter plasma is detected.

In one embodiment, the terahertz radiation emitted by the emitter plasma comprises a terahertz wave pulse, in accordance with an aspect of the present invention. Pulsed terahertz wave spectroscopy is capable of sensing at short ranges a number of substances, including compounds from which improvised explosive devices (IEDs) may be made. For example, the compound RDX has been identified from the terahertz radiation emitted by plasma induced in a sample of RDX at distances up to 30 meters away in good weather. However, the detection range of terahertz radiation may decrease to less than 10 meters in humid atmospheric conditions because the propagation of a terahertz wave in air is largely limited by water vapor absorption. For example, the attenuation of terahertz waves through the atmosphere is greater than 100 dB/km, even when the humidity level is only 20% around room temperature. Measurements of the attenuation effect at humidity levels from 3% to 100% indicate that, in ambient air, it may not be practical to get useful terahertz spectroscopy information from a terahertz wave traveling more than 100 meters. On the other hand, optical pulses (i.e. pulses of visible light, for example) have a significantly lower attenuation (on the order of 0.01 dB/km) than terahertz waves in the air. Because optical pulses may be used to induce the emission of terahertz waves by ionizing at least a portion of a targeted object and to sense the incidence of the emitted terahertz waves, in accordance with an aspect of the present invention, optical radiation may be used advantageously in terahertz spectroscopy both to induce the emission of a terahertz wave from a targeted object and to detect the emitted terahertz wave from a remote location to solve the problem of high attenuation of terahertz radiation in the atmosphere. Through the use of optical-wavelength radiation in these ways, the effective range at which terahertz spectroscopy can detect explosive materials, for example, may be increased.

In one aspect, the present invention provides a technique for analyzing a targeted object for substances of interest, including explosives and explosive related compounds, from a distance. The technique utilizes electromagnetic radiation to ionize at least a portion of the targeted object and induce an emission of terahertz radiation from the resulting emitter plasma. The terahertz radiation emitted by the plasma of the targeted object may be detected by detecting optical radiation that results from an interaction of the terahertz radiation with an optical probe beam. In another aspect, the present invention provides a technique that utilizes a combination of a pulsed laser beam, focused on a targeted object to ionize at least a portion of the targeted object, and detected optical radiation, which includes a manifestation of the spectrum of terahertz radiation induced by the phase transformation in the targeted object, to detect explosives and explosive related compounds from a distance. In one embodiment, a pulsed laser provides an optical pump beam for producing an emitter plasma by ionizing the target object about the focal point of the optical pump beam. The resulting emitter plasma emits a terahertz wave, and an optical probe beam is focused in proximity to the targeted object. The resulting plasma of ionized ambient air is utilized as terahertz wave sensor. Since terahertz waves are detected near the targeted object, attenuation due to water vapor absorption is reduced. Coherent detection of the terahertz wave using ionized air as a terahertz wave sensor has been demonstrated in experiments by the inventors.

In one embodiment, femtosecond (fs) optical pulses from a laser source are utilized for producing the emitter plasma in the targeted object and the sensor plasma in an ambient gas such as air. The emitter plasma resulting from a phase transformation in the targeted object emits terahertz radiation, and the sensor plasma detects the terahertz wave that results from the ionization of at least a portion of the targeted object. An explosive or related compound is detected by identifying a characteristic spectral fingerprint of the material in the terahertz wave emitted by the emitter plasma and detected by the sensor plasma.

FIG. 1 illustrates one embodiment of a system 101 for remotely analyzing an object, wherein an optical probe beam is focused in a plasma induced by illuminating at least a portion of a targeted object with electromagnetic radiation, in accordance with an aspect of the present invention. System 101 comprises source-and-detector unit 102 for inducing and detecting terahertz radiation from a targeted object, a spectroscopy signal processing unit 117, and an imaging signal processing unit 118. Source-and-detector unit 102 for inducing and detecting terahertz radiation from a targeted object includes electromagnetic radiation source 103, laser source 107, lens 108, nonlinear optical crystal 109, such as a β-barium borate (BBO) crystal, lens 112, optical filter 113, and optical detector 115. Electromagnetic-radiation source 103 illuminates at least a portion of a targeted object 105 with electromagnetic radiation 104, which is directed toward the targeted object, to induce a phase transformation in the targeted object, wherein the phase transformation produces an emitter plasma 106, which emits terahertz radiation. Lens 108 focuses optical probe beam 110 from laser source 107 in emitter plasma 106, and the interaction of the optical probe beam 110 with terahertz radiation in emitter plasma 106 produces resultant optical radiation 111. That is, the same plasma that emits terahertz radiation, as a result of a phase transformation induced in the targeted object, is also used to sense the terahertz radiation. Optical detector 115 detects a component of resultant optical radiation 114 that is passed by filter 113. For example, the detected component may comprise a second harmonic of the optical probe beam 104. A lens 112 may be utilized to focus resultant optical radiation 111 on optical detector 115.

Optical detector 115 provides signal 116 in response to the detected component of resultant optical radiation 111. Spectroscopy signal processing unit 117 analyzes signal 116, which is provided by optical detector 115.

Imaging signal processing unit 118 is coupled to spectroscopy signal processing unit 117. Imaging signal processing unit 118 produces a spectroscopic image of the targeted object, or a feature thereof, from an output of spectroscopy signal processing unit 117. Spectroscopy signal processing unit 117 and imaging signal processing unit 118 may comprise programs of instructions that are executable on a computer, microprocessor, or digital signal processor (DSP) chip, for example.

Figure 2:
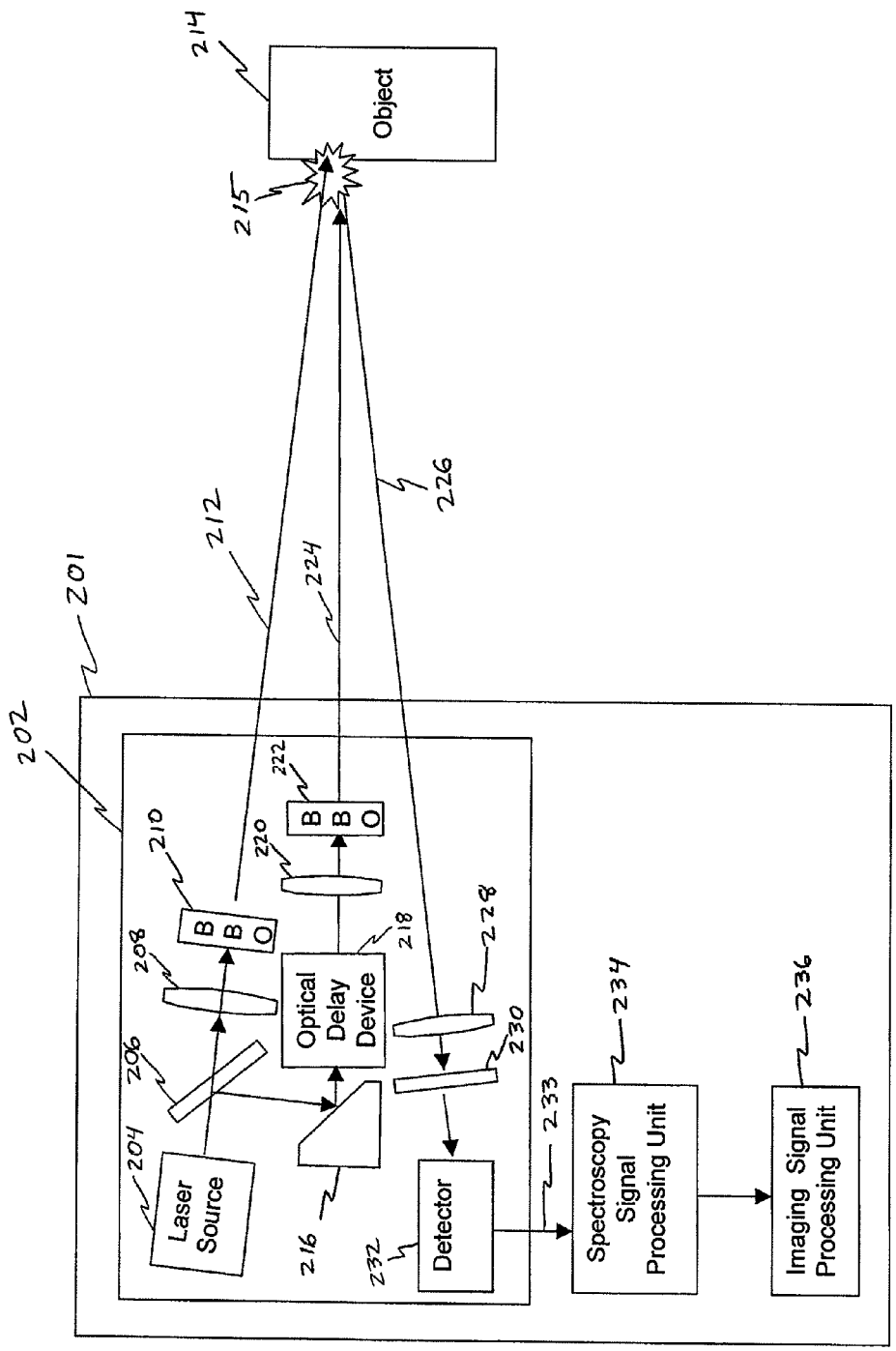
FIG. 2 illustrates another embodiment of a system for remotely analyzing an object, wherein an optical probe beam is focused in a plasma induced by illuminating at least a portion of a targeted object with an optical-wavelength pump beam, in accordance with an aspect of the present invention.

FIG. 2 illustrates another embodiment of a system 201 for remotely analyzing an object, wherein an optical probe beam is focused in a plasma induced by illuminating at least a portion of a targeted object with an optical-wavelength pump beam, in accordance with an aspect of the present invention. System 201 comprises optical system 202, spectroscopy signal processing unit 234, and imaging signal processing unit 236. Optical system 202 comprises a source of an optical pump beam, means for focusing the optical pump beam, a source of an optical probe beam, means for focusing an optical probe beam, and an optical detector. The optical pump beam illuminates at least a portion of a targeted object to induce a phase transformation in the targeted object. The phase transformation produces an emitter plasma, which emits terahertz radiation. A source of an optical probe beam provides an optical probe beam that is focused in the resulting emitter plasma. As a result of an interaction, in the emitter plasma, of the optical probe beam and the terahertz radiation resulting from the phase transformation in the targeted object, the emitter plasma emits a resultant optical beam. The resultant optical beam emitted by the emitter plasma is detected by an optical detector such as a photomultiplier detector or a photodiode.

In the embodiment of FIG. 2, the source of an optical pump beam comprises laser source 204, beamsplitter 206, and lens 208. An optical-wavelength beam that is provided by the laser source and passed by beamsplitter 206 is focused by lens 208 to produce optical pump beam 212. In this embodiment, optical pump beam 212 induces a phase transformation in targeted object 214 to produce emitter plasma 215. As result of the phase transformation, emitter plasma 215 emits terahertz radiation. Optionally, nonlinear optical crystal 210 may follow lens 208. In one example, nonlinear optical crystal 210 comprises a β-barium borate (BBO) crystal.

The system of FIG. 2 also provides optical probe beam 224, which is focused in emitter plasma 215 produced by the phase transformation in the targeted object. Optical probe beam 224 is produced by laser source 204, beamsplitter 206, mirror 216, optical delay device 218, and lens 220. Beamsplitter 206 directs a portion of the optical radiation from laser source 204 to mirror 216. Mirror 216 directs incident optical radiation from the beamsplitter to optical delay device 218 and lens 220, which focuses the optical radiation from mirror 216 to provide optical probe beam 224. One example of optical delay device 218 comprises a series of mirrors arranged to increase the length of the optical radiation's propagation path. Optionally, nonlinear optical crystal 222 may follow lens 220. In one example, nonlinear optical crystal 222 comprises a β-barium borate (BBO) crystal.

As a result of the interaction of optical probe beam 224 and terahertz radiation in emitter plasma 215, a resultant optical radiation 226 is emitted from the emitter plasma. Resultant optical radiation 226, comprising, for example, a second harmonic frequency of the optical probe beam's fundamental frequency, is concentrated by lens 228 and filtered by filter 230 to attenuate background optical radiation. Optical detector 232 detects a second harmonic component of resultant optical radiation 226 that is passed by filter 230. Optical detector 232 may comprise a photomultiplier detector, for example, or a photodiode, as another example.

Optical detector 232 provides signal 233 in response to the detected component of resultant optical radiation 226. Spectroscopy signal processing unit 234 analyzes signal 233, which is provided by optical detector 233. Imaging signal processing unit 236 is coupled to spectroscopy signal processing unit 234. Imaging signal processing unit 236 produces a spectroscopic image of the targeted object, or a feature thereof, from an output of spectroscopy signal processing unit 234. Spectroscopy signal processing unit 234 and imaging signal processing unit 236 may comprise programs of instructions that are executable on a computer, microprocessor, or digital signal processor (DSP) chip, for example.

Figure 3:
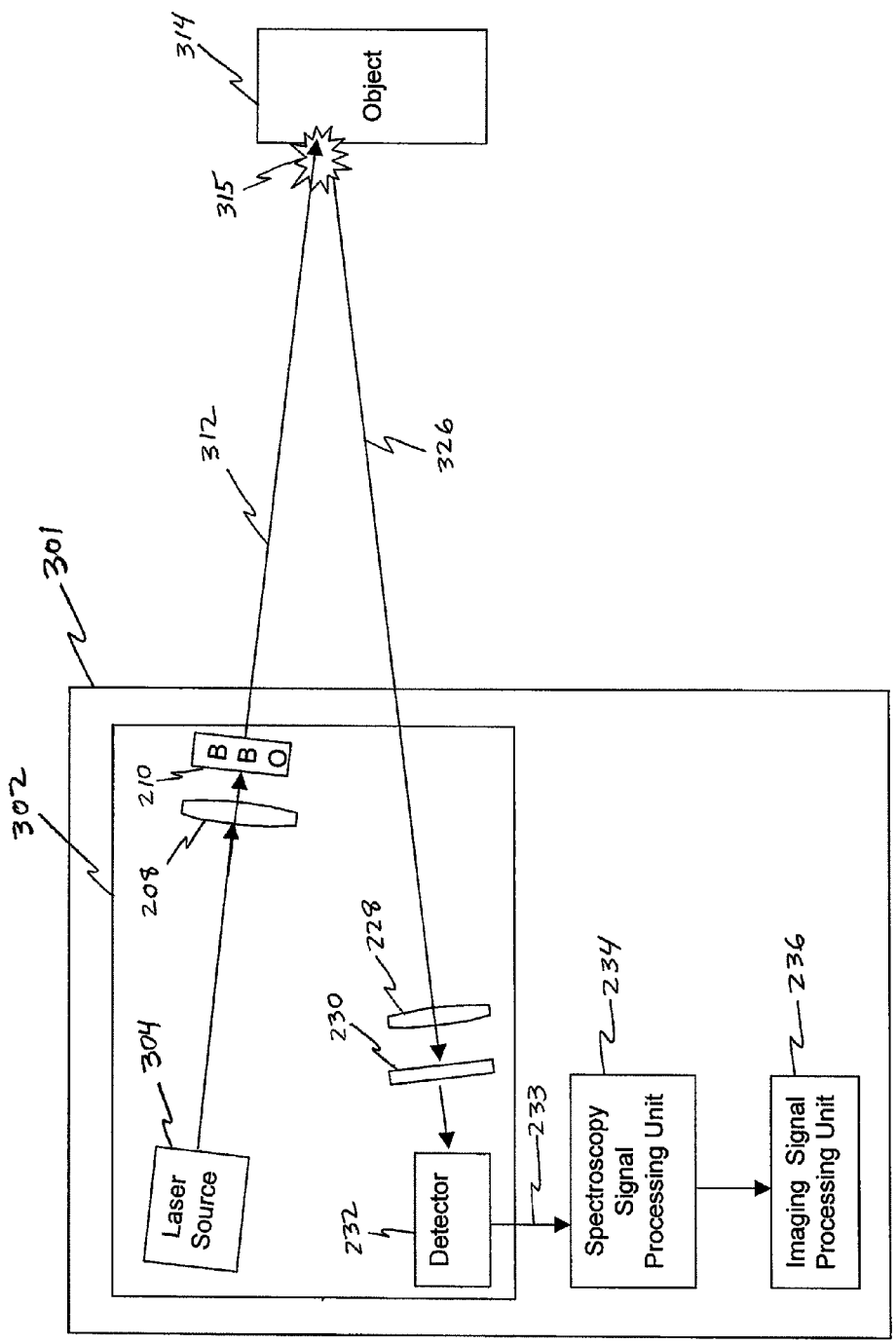
FIG. 3 illustrates an embodiment of a system for remotely analyzing an object, wherein the system comprises a pulsed laser source, in accordance with an aspect of the present invention.

FIG. 3 illustrates an embodiment of a system 301 for remotely analyzing an object, wherein the system utilizes a pulsed laser source, in accordance with an aspect of the present invention.

System 301 comprises optical system 302, spectroscopy signal processing unit 234, and imaging signal processing unit 236. Optical system 302 comprises pulsed laser source 304, lens 208, and nonlinear optical crystal 210. Pulsed laser source provides pulses of optical-wavelength radiation. Lens 208 focuses the pulses of optical-wavelength radiation to produce optical beam 312. The optical beam illuminates at least a portion of a targeted object 314 with one or more pulses of optical wavelength radiation to induce a phase transformation in the targeted object. The phase transformation produces emitter plasma 315, which emits terahertz radiation. Optical beam 312 also comprises one or more optical probe pulses, comprising subsequent pulses of optical wavelength radiation from pulsed laser source 304 that are focused in emitter plasma 315. As a result of an interaction of the optical probe pulses and the terahertz radiation resulting from the phase transformation in the targeted object, emitter plasma 315 emits a resultant optical radiation 326.

Resultant optical radiation 326, comprising, for example, a second harmonic frequency of an optical probe pulse's fundamental frequency, is concentrated by lens 228 and filtered by filter 230 to attenuate background optical radiation. Optical detector 232 detects a second harmonic component of resultant optical radiation 326 that is passed by filter 230. Optical detector 232 may comprise a photomultiplier detector, for example, or a photodiode, as another example.

Optionally, nonlinear optical crystal 210 may follow lens 208 to induce the emitter plasma to emit stronger terahertz radiation or to produce a stronger resultant optical radiation 326 from an interaction in emitter plasma 315 of one or more optical probe pulses with terahertz radiation emitted as a result of the induced phase transformation in the targeted object. In one example, nonlinear optical crystal 210 comprises a β-barium borate (BBO) crystal.

Figure 4:
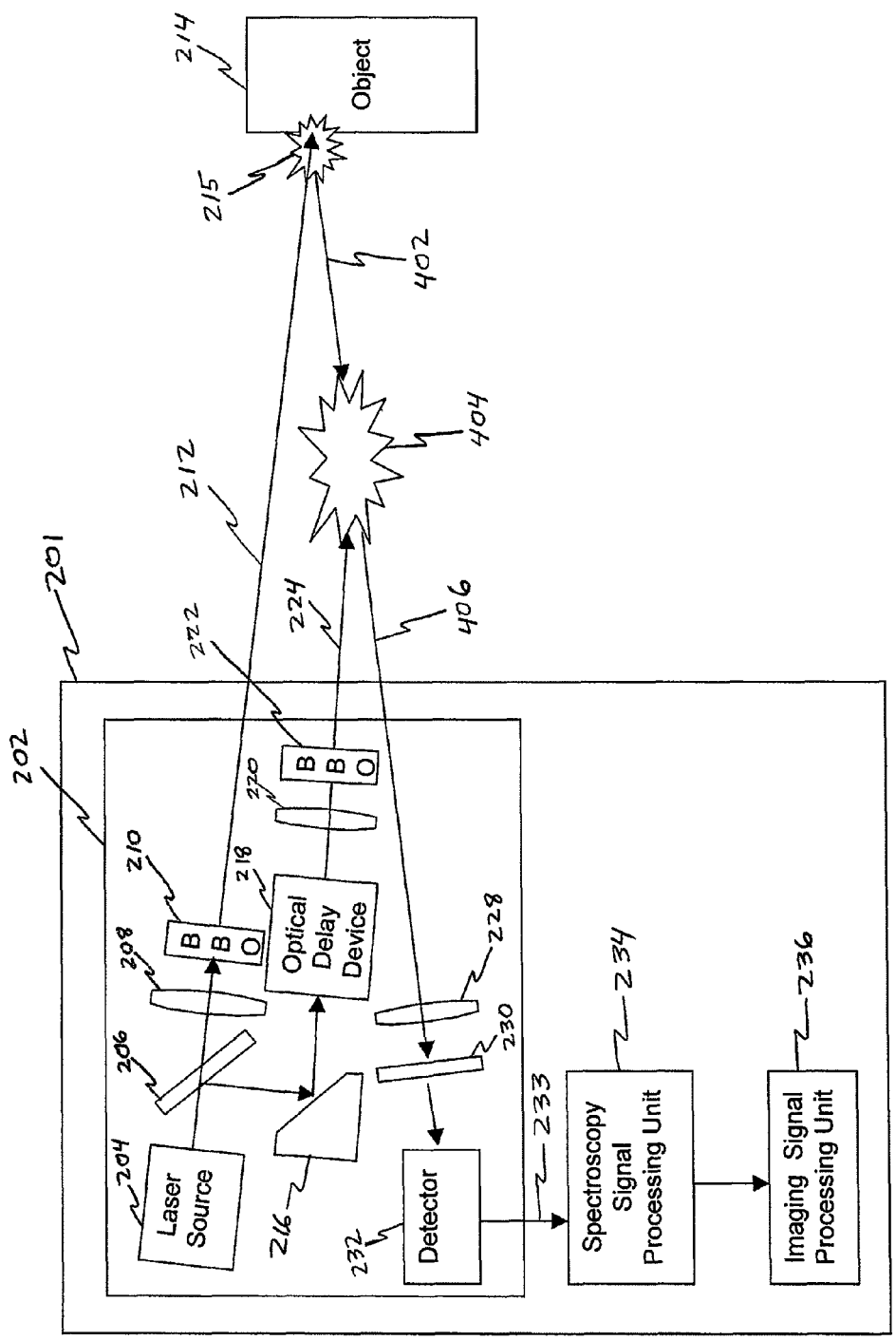
FIG. 4 illustrates another embodiment of a system for remotely analyzing an object, wherein an optical pump beam induces a phase transformation in the targeted object, and wherein a sensor plasma is utilized to detect terahertz radiation emitted by an emitter plasma resulting from the phase transformation, in accordance with an aspect of the present invention.

FIG. 4 illustrates another embodiment of a system 201 for remotely analyzing an object, wherein an optical pump beam induces a phase transformation in the targeted object, and wherein a sensor plasma is utilized to detect terahertz radiation emitted by an emitter plasma resulting from the phase transformation, in accordance with an aspect of the present invention. System 201 comprises optical system 202, spectroscopy signal processing unit 234, and imaging signal processing unit 236. Optical system 202 comprises a source of an optical pump beam, means for focusing the optical pump beam, a source of an optical probe beam, means for focusing an optical probe beam, and an optical detector. The means for focusing the optical pump beam may comprise a lens or concave mirror, for example. The optical pump beam illuminates at least a portion of a targeted object to induce a phase transformation in the targeted object. The phase transformation produces an emitter plasma, which emits terahertz radiation. A source of an optical probe beam provides a focused optical probe beam for ionizing a volume of ambient gas to produce a sensor plasma. The sensor plasma emits a resultant optical beam as a result of an interaction of the optical probe beam and the terahertz radiation resulting from the phase transformation in the targeted object. The resultant optical beam emitted by the sensor plasma is detected by an optical detector such as a photomultiplier detector or a photodiode.

In the embodiment of FIG. 4, the source of an optical pump beam comprises laser source 204, beamsplitter 206, and lens 208. A portion of an optical-wavelength beam that is provided by laser source 204 is passed by beamsplitter 206 to lens 208. Lens 208 focuses the portion of the optical-wavelength beam passed by beamsplitter 206 to produce optical pump beam 212. In this embodiment, optical pump beam 212 induces a phase transformation in targeted object 214 to produce emitter plasma 215. As result of the phase transformation, emitter plasma 215 emits terahertz radiation 402.

The system of FIG. 4 also provides optical probe beam 224, which ionizes the ambient gas in a volume to produce sensor plasma 404. Optical probe beam 224 is produced by laser source 204, beamsplitter 206, mirror 216, optical delay device 218, and lens 220. Beamsplitter 206 directs a portion of the optical radiation from laser source 204 to mirror 216. Mirror 216 directs incident optical radiation from the beamsplitter to optical delay device 218 and lens 220, which focuses the optical radiation from mirror 216 to provide optical probe beam 224. One example of optical delay device 218 comprises a series of mirrors arranged to increase the length of the optical radiation's propagation path. Optionally, nonlinear optical crystal 222 may follow lens 220. In one example, nonlinear optical crystal 222 comprises a β-barium borate (BBO) crystal.

As a result of the interaction of optical probe beam 224 and terahertz radiation 402 in sensor plasma 404, a resultant optical radiation 406 is emitted from the sensor plasma. Resultant optical radiation 406, comprising, for example, a second harmonic frequency of the optical probe beam's fundamental frequency, is concentrated by lens 228 and filtered by filter 230 to attenuate background optical radiation. Optical detector 232 detects a second harmonic component of resultant optical radiation 406 that is passed by filter 230. Optical detector 232 may comprise a photomultiplier detector, for example, or a photodiode, as another example.

Optical detector 232 provides signal 233 in response to the detected component of resultant optical radiation 406. Spectroscopy signal processing unit 234 analyzes signal 233, which is provided by optical detector 233. Imaging signal processing unit 236 is coupled to spectroscopy signal processing unit 234. Imaging signal processing unit 236 produces a spectroscopic image of the targeted object, or a feature thereof, from an output of spectroscopy signal processing unit 234. Spectroscopy signal processing unit 234 and imaging signal processing unit 236 may comprise programs of instructions that are executable on a computer, microprocessor, or digital signal processor (DSP) chip, for example.

In the embodiment of FIG. 4, the optical pump beam source may also include a nonlinear optical crystal 210, such as a β-barium borate (BBO) crystal, to induce the emitter plasma to emit stronger terahertz radiation. Also, nonlinear optical crystal 222 may be positioned after lens 220 to induce the sensor plasma to emit a stronger second harmonic component of resultant optical radiation 406.

Figure 5:
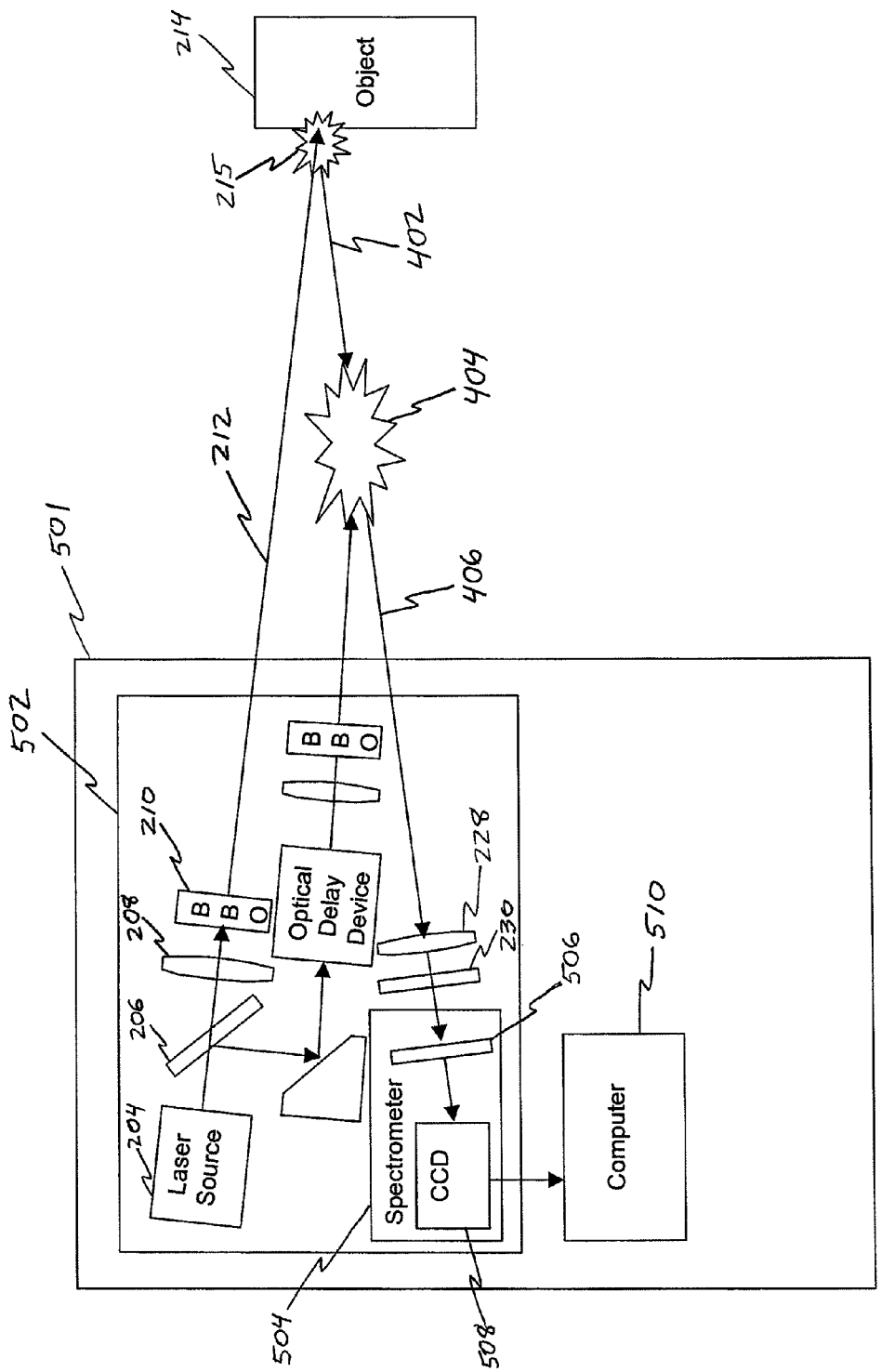
FIG. 5 illustrates an embodiment of a system for remotely analyzing an object, wherein a sensor plasma and a spectrometer are utilized to detect terahertz radiation emitted as a result of a phase transformation induced in the targeted object, and wherein a computer is utilized for spectroscopy signal processing, in accordance with an aspect of the present invention.

FIG. 5 illustrates an embodiment of a system 501 for remotely analyzing an object, wherein a sensor plasma and a spectrometer are utilized to detect terahertz radiation emitted as a result of a phase transformation induced in the targeted object, and wherein a computer is utilized for spectroscopy signal processing, in accordance with an aspect of the present invention. System 501 comprises optical system 502 and computing system 510. Optical system 502 comprises an example of optical system 202 of FIG. 2, wherein optical detector 232 comprises spectrometer 504. In one example of this embodiment, spectrometer 504 comprises electro-optical charge coupled device 508. Electro-optical charge coupled device 508 is coupled to computing system 510, which executes one or more programs of instructions for spectroscopy signal processing and image signal processing to process the signal provided by the electro-optical charge coupled device. In another example, spectrometer 504 comprises grating 506 and electro-optical charge coupled device 508. In this example, grating 506 disperses light, which comprises a component of resultant optical radiation 406 that is passed by filter 230, onto electro-optical charge coupled device 508.

Figure 6:
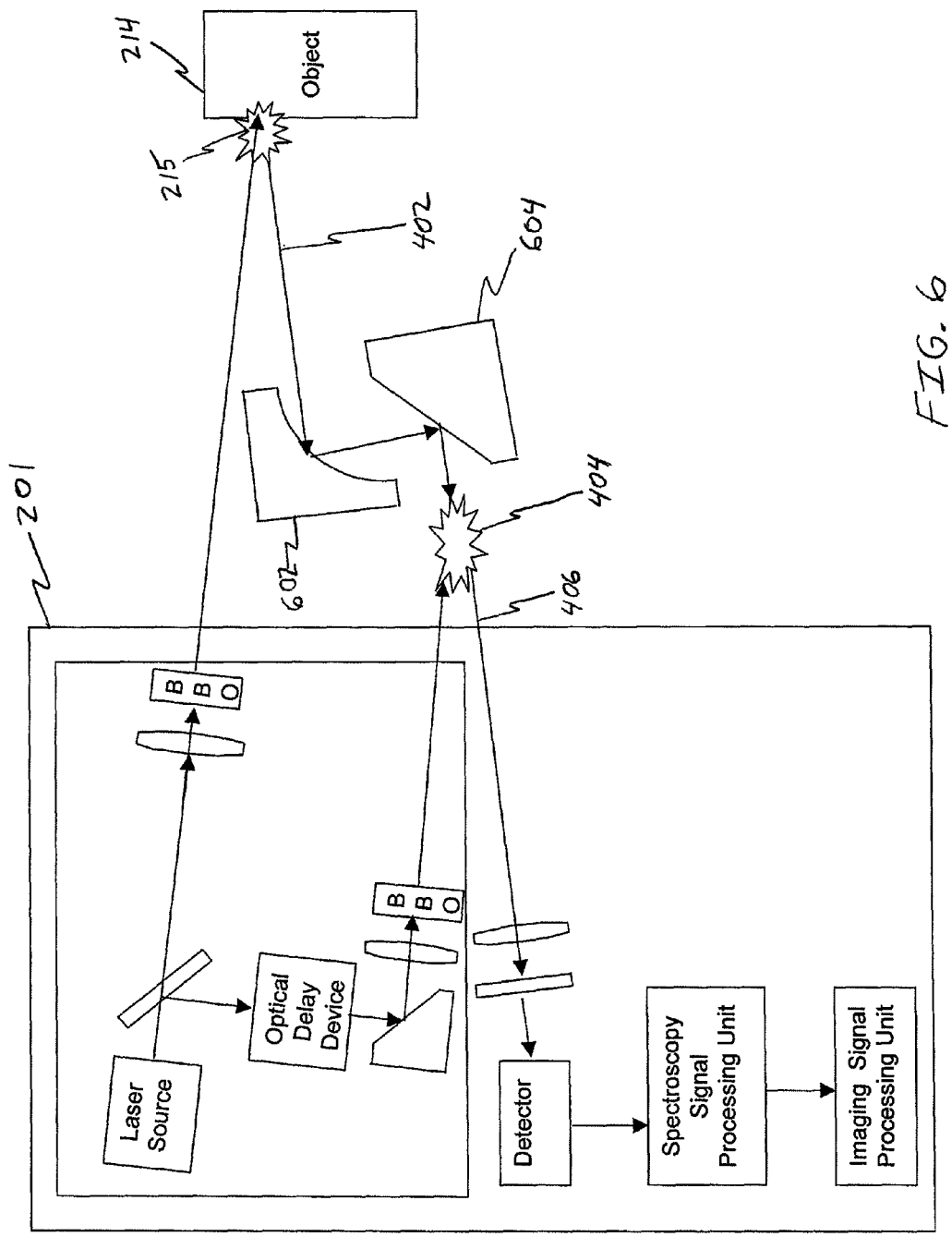
FIG. 6 illustrates an embodiment of a system for analyzing an object, in accordance with an aspect of the present invention, wherein terahertz radiation emitted by an induced plasma is concentrated by a parabolic mirror to facilitate detection of the terahertz radiation in a sensor plasma.

FIG. 6 illustrates an embodiment of a system for analyzing an object, in accordance with an aspect of the present invention, wherein terahertz radiation emitted by an induced plasma is concentrated by a parabolic mirror to facilitate detection of the terahertz radiation in a sensor plasma. The system illustrated in FIG. 6 comprises system 201 of FIG. 4, parabolic mirror 602, and mirror 604. In the embodiment of FIG. 6, parabolic mirror 602 concentrates terahertz radiation 402 emitted by emitter plasma 215, which is produced as a result of an optical pump beam from system 201 inducing a phase transformation in targeted object 214. The concentrated terahertz radiation is reflected by mirror 604 toward sensor plasma 404, and resultant optical radiation 406 is emitted from the sensor plasma as a result of the interaction in sensor plasma 404 of the concentrated terahertz radiation with the optical probe beam provided by system 201.

Figure 7:
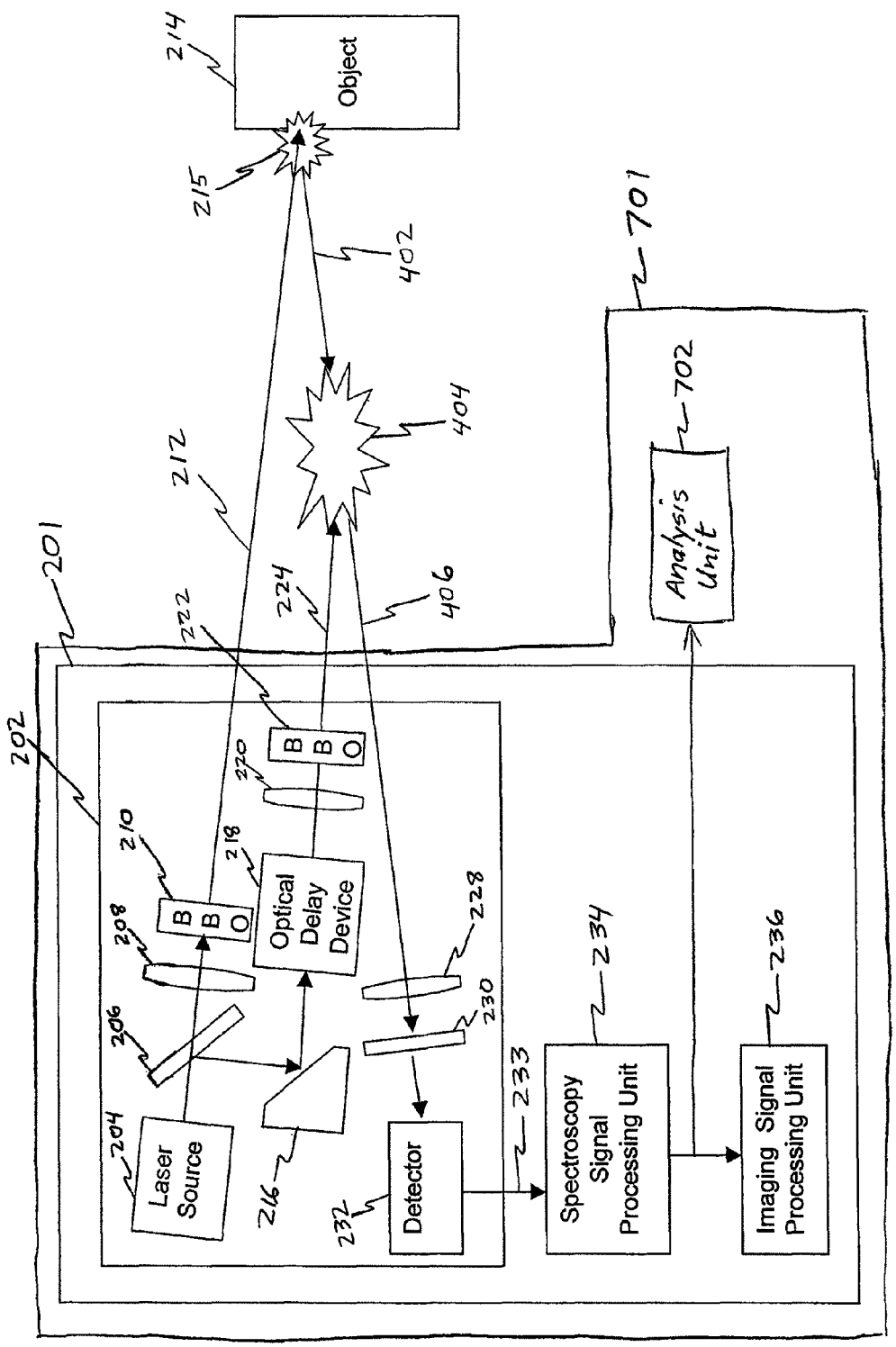
FIG. 7 illustrates an embodiment of a system for analyzing an object, wherein the system includes an analysis unit for processing spectroscopy analysis information, in accordance with an aspect of the present invention.

In an embodiment illustrated in FIG. 7, a system 701 for remotely analyzing a targeted object comprises system 201 of FIG. 4 and analysis unit 702, in accordance with an aspect of the invention. Analysis unit 702 comprises a decision unit for determining whether a substance is present in the targeted object from the spectroscopy analysis information provided by spectroscopy signal processing unit 234 in one example. The analysis unit utilizes a manifestation of the spectrum of the terahertz radiation, which was emitted by the emitter plasma, in the spectroscopy analysis information to determine whether a substance of interest is present in the targeted object. In another example, analysis unit 702 comprises an identification unit for identifying a substance of the targeted object from the spectroscopy analysis information provided by spectroscopy signal processing unit 234. In this example, the analysis unit utilizes a manifestation of the spectrum of the terahertz radiation, which was emitted by the emitter plasma, in the spectroscopy analysis information to identify a substance of the targeted object. In one embodiment, the analysis unit compares the manifestation of the spectrum of the terahertz radiation in the spectroscopy analysis information to the known characteristic spectral fingerprints of one or more substances of interest.

Additional details of a technique for utilizing a plasma to detect terahertz radiation emitted as a result of inducing a phase transformation in a targeted object are provided below.

In one aspect of the present invention, an ionized ambient gas is utilized as a sensor for detecting terahertz radiation. One example of an ambient gas that may be utilized is air. Using air as a terahertz wave sensor advantageously provides flexibility in selecting a sensing location because air surrounds targeted objects to be analyzed in many environments of interest. Terahertz waves may be detected in ionized air with a third order nonlinear optical process by exploiting the third order nonlinear susceptibility of ionized air. As will be appreciated by one of ordinary skill in the art, there are several possible techniques to provide a third order nonlinear optical process in air. In one example, an optical probe pulse interacts with the incident terahertz wave in a sensor plasma comprising air ionized by the optical probe pulse. The interaction of the optical probe pulse and incident terahertz wave in the sensor plasma produces a resultant optical pulse comprising optical radiation at the second harmonic of the fundamental frequency of the probe pulse. The measurement of the polarization rotation of optical radiation is known, and it provides a sensitive indirect detection technique for the terahertz waves by measuring the polarization change.

Since a nonlinear interaction of ionized air, incident terahertz waves and an optical probe pulse generates a second harmonic of the probe pulse, another technique for detection of terahertz radiation comprises detecting this second harmonic optical radiation. In one embodiment, the resultant second harmonic optical radiation, which is modulated by the incident terahertz wave, comprises frequencies that are different from the frequencies of the probe pulses. This technique advantageously makes it possible to detect weak sensor plasma output signals because strong background interference from the probe beam may be readily quenched due to the difference in the frequencies of the probe beam and the component of the sensor plasma's output signal being detected.

The expression below illustrates the proportional relationship of the electric field strength, $E_{2\omega}(t, \tau)$, of the resulting second harmonic optical radiation to the electric field of the incident terahertz wave and the electric field of the probe beam for incoherent detection:

$$E_{2\omega}(t,\tau) \propto E_{Terahertz}(t-\tau)E_\omega(t)E_\omega(t) = E_{Terahertz}(t-\tau)I_\omega(t),$$

where $E_\omega(t, \tau)$ is the electric field strength of the optical probe beam having a frequency $\omega$ and where $E_{Terahertz}(t-\tau)$ is the electric field strength of the incident terahertz wave. The electric field strength, $E_{2\omega}(t, \tau)$, of the second harmonic optical radiation emitted by the sensor plasma is also proportional to the intensity of the probe beam ($I_\omega(t)$) because the square of the electric field $E_\omega(t)$ of the optical probe beam is proportional to its intensity. As illustrated by the above expression, two fundamental-frequency optical photons and one terahertz photon interact in the sensor plasma to produce a second harmonic photon. The time-resolved second harmonic optical intensity is detected to obtain the information carried by the incident terahertz wave. From the expression $E_{2\omega}(t) \propto E_{Terahertz}(t-\tau)I_\omega(t)$, it is apparent that the intensity of the second harmonic $I_{2\omega}(t)$ emitted by the sensor plasma in response to the incident probe beam and terahertz wave is proportional to the square of the intensity of the optical probe beam; that is $I_{2\omega}(t) \propto I_{Terahertz}(t-\tau)I_\omega^2(t)$, where $I_{Terahertz}(t-\tau)$ is the intensity of the incident terahertz wave. This indicates that a strong probe beam, having fundamental frequency $\omega$, may greatly improve the detection of a weak terahertz wave by increasing the intensity of the second harmonic optical radiation emitted by the sensor plasma.

In another embodiment, a technique for coherent detection of terahertz radiation is utilized. In this embodiment, terahertz radiation to be detected is mixed nonlinearly with a probe beam that is derived from the same pump beam that induced the terahertz radiation. As a result, the time delays of the optical probe beam and terahertz radiation are correlated. Also, a strong fundamental probe beam creates a second harmonic background. Under these conditions, the second harmonic optical radiation emitted as a result of nonlinear interaction of the optical probe beam and incident terahertz radiation in the sensor plasma has an intensity $I_{2\omega}$ that may be characterized by the expression below, which illustrates the proportional relationship of the intensity of the resulting second harmonic optical radiation, $I_{2\omega}(t, \tau)$, to the electric field of the incident terahertz wave and the square of the intensity of the probe beam for coherent detection:

$$I_{2\omega} \propto (I_\omega)^2 E_{Terahertz}$$

where $I_\omega$ is the intensity of the optical probe beam having a frequency $\omega$ and where $E_{Terahertz}$ is the magnitude of the electric field of the incident terahertz wave. The intensity $I_{2\omega}$ of the second harmonic optical radiation output by the sensor plasma is proportional to the square of the intensity of the probe beam. The intensity $I_{2\omega}$ of the second harmonic optical radiation output by the sensor plasma is also proportional to the magnitude of the electric field of the incident terahertz wave. Experimental measurements indicate that coherent detection is feasible and that the intensity of the optical radiation emitted by the sensor plasma is related to the probe beam and incident terahertz radiation as shown in the expression above.

Since it has been observed in experiments that the lifetime of laser-induced plasma may exceed 150 picoseconds, the same plasma that emits terahertz radiation, as a result of a phase transformation induced in the targeted object, may be used subsequently as a sensor plasma for the terahertz wave detection in an embodiment of a technique to analyze a remotely-located object. It is possible to send a relatively weak probe beam to an existing emitter plasma to take advantage of a large resonance third-order nonlinearity, which was produced by the optical pump beam that induced the phase transformation producing the emitter plasma, to detect a terahertz wave generated by the plasma.

With respect to an emission of a terahertz wave as a result of a phase transformation in a substance that is induced by a fundamental optical wave and its second harmonic, the magnitude of the terahertz wave's electric field has been found to increase linearly with the energy of the fundamental optical wave once the energy of the fundamental optical wave exceeds a threshold. In contrast, it has been found that the electric field of the resulting terahertz wave increases approximately with the square root of the energy of the second harmonic optical beam once the energy of the fundamental optical wave exceeds a threshold. It has been observed that this energy threshold is very close to the energy threshold for ionizing a substance to which the optical radiation is directed.

It was also found that the electric field strength of a terahertz wave induced by a fundamental optical pulse and a second-harmonic optical pulse may be changed by controlling the polarizations, intensities, and phases of the fundamental and second harmonic optical excitation pulses relative to each other.

As a consequence of the observed behaviors of the sensor and emitter plasmas, in an embodiment that utilizes a nonlinear optical crystal to produce an optical pump beam or an optical probe beam or both, in accordance with aspects of the invention, a stronger optical component of resultant radiation, which includes a manifestation of the characteristic terahertz spectrum of a substance of the targeted object, may advantageously be obtained.

Further details of a technique for utilizing a plasma, which is induced by an optical beam, to detect terahertz radiation are provided in the following patent application, which is hereby incorporated herein by reference in its entirety: U.S. Ser. No.

11/610,824 entitled "Method of Analyzing a Remotely-Located Object Utilizing an Optical Technique to Detect Terahertz Radiation", filed Dec. 14, 2006.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

What is claimed is:

1. A method of analyzing a remotely-located object comprising:

illuminating at least a portion of a targeted object with electromagnetic radiation to induce a phase transformation in the targeted object, wherein the phase transformation produces an emitter plasma, the emitter plasma emitting terahertz radiation;

focusing an optical probe beam in the emitter plasma; and detecting an optical component of resultant radiation produced from an interaction of the focused optical probe beam and the terahertz radiation in the emitter plasma.

2. The method of claim 1 wherein the optical component of the resultant radiation comprises a harmonic of a fundamental frequency of the optical probe beam.

3. The method of claim 1 wherein the optical probe beam comprises an optical radiation component having a fundamental frequency and a harmonic optical radiation component having a frequency that is harmonically related to the fundamental frequency.

4. The method of claim 1 further comprising processing the optical component of resultant radiation detected by the step of detecting to produce spectroscopy analysis information.

5. The method of claim 4 further comprising producing a spectroscopy image from the spectroscopy analysis information.

6. The method of claim 1 wherein the electromagnetic radiation comprises at least one first pulse of optical wavelength radiation and at least one second pulse of optical wavelength radiation, wherein the least one second pulse is delayed relative to the at least one first pulse.

7. The method of claim 1 wherein the targeted object comprises at least one of an explosive material that is harmful to humans, a biological agent that is harmful to humans, and a chemical agent that is harmful to humans.

8. The method of claim 1 wherein the targeted object is located more than thirty meters away from a source of the electromagnetic radiation.

9. The method of claim 1 wherein the detecting of the optical component of resultant radiation comprises coherent detecting.

10. The method of claim 9 wherein the coherent detecting comprises correlating a time delay of the optical probe beam with a time delay of the terahertz radiation.

11. A system for analyzing a remotely-located object comprising:

a source of electromagnetic radiation;

means for focusing the electromagnetic radiation to produce focused electromagnetic radiation that illuminates at least a portion of a targeted object to induce a phase transformation in the targeted object, wherein the phase transformation produces an emitter plasma, the emitter plasma emitting terahertz radiation;

a source of an optical probe beam;

means for focusing the optical probe beam in the emitter plasma; and an optical detector for detecting an optical component of resultant radiation produced from an interaction of the focused optical probe beam and the terahertz radiation in the emitter plasma.

12. The system of claim 11 wherein the optical component of the resultant radiation comprises a harmonic of a fundamental frequency of the optical probe beam.

13. The system of claim 11 wherein the optical probe beam comprises an optical radiation component having a fundamental frequency and a harmonic optical radiation component having a frequency that is harmonically related to the fundamental frequency, and wherein the optical detector further comprises an optical filter for attenuating a component of the resultant radiation comprising the fundamental frequency of the optical probe beam.

14. The system of claim 11 further comprising a spectroscopy signal processing unit for analyzing the optical component of resultant radiation detected by the optical detector.

15. The system of claim 11 wherein the electromagnetic radiation comprises at least one first pulse of optical wavelength radiation and at least one second pulse of optical wavelength radiation, wherein the least one second pulse is delayed relative to the at least one first pulse.

16. The system of claim 11 wherein the targeted object comprises at least one of an explosive material that is harmful to humans, a biological agent that is harmful to humans, and a chemical agent that is harmful to humans.

17. The system of claim 11 wherein the targeted object is located more than thirty meters away from a source of the electromagnetic radiation.

18. The system of claim 11 wherein the optical detector comprises a coherent optical detector.

19. The system of claim 18 wherein the coherent optical detector further comprises a correlator adapted to correlate a time delay of the optical probe beam with a time delay of the terahertz radiation.

* * * * *